United States Patent
Walters et al.

(10) Patent No.: US 7,673,507 B2
(45) Date of Patent: Mar. 9, 2010

(54) REAL TIME VISCOMETER

(75) Inventors: Harold G. Walters, Duncan, OK (US); Billy Ray Slabaugh, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 366 days.

(21) Appl. No.: 11/619,801

(22) Filed: Jan. 4, 2007

(65) Prior Publication Data

US 2008/0163681 A1     Jul. 10, 2008

(51) Int. Cl.
*E21B 47/08* (2006.01)
(52) U.S. Cl. .................................. 73/152.55
(58) Field of Classification Search ............... 73/152.55
See application file for complete search history.

(56) References Cited

U.S. PATENT DOCUMENTS

| | | | | |
|---|---|---|---|---|
| 5,080,809 A | * | 1/1992 | Stahl et al. | 507/221 |
| 5,133,624 A | * | 7/1992 | Cahill | 405/129.4 |
| 5,186,257 A | * | 2/1993 | Stahl et al. | 166/270.1 |
| 5,382,371 A | * | 1/1995 | Stahl et al. | 507/221 |
| 5,393,439 A | * | 2/1995 | Laramay et al. | 507/211 |
| 5,990,052 A | * | 11/1999 | Harris | 507/214 |
| 6,030,928 A | * | 2/2000 | Stahl et al. | 507/121 |
| 6,176,323 B1 | * | 1/2001 | Weirich et al. | 175/40 |
| 6,206,108 B1 | * | 3/2001 | MacDonald et al. | 175/24 |
| 6,439,310 B1 | * | 8/2002 | Scott et al. | 166/308.1 |
| 6,782,735 B2 | | 8/2004 | Walters et al. | |
| 6,861,393 B2 | * | 3/2005 | Temple et al. | 507/119 |
| 6,989,353 B2 | * | 1/2006 | Temple et al. | 507/119 |
| 7,351,681 B2 | * | 4/2008 | Reddy et al. | 507/219 |
| 7,392,842 B2 | | 7/2008 | Morgan et al. | |
| 7,423,258 B2 | * | 9/2008 | DiFoggio et al. | 250/269.1 |
| 2008/0141767 A1 | * | 6/2008 | Raghuraman et al. | 73/152.55 |
| 2008/0230220 A1 | | 9/2008 | Morgan et al. | |

\* cited by examiner

*Primary Examiner*—Hezron Williams
*Assistant Examiner*—Rodney T Frank
(74) *Attorney, Agent, or Firm*—John W. Wustenberg; Baker Botts, LLP

(57) ABSTRACT

An apparatus for predicting a downhole viscosity of a treating fluid has an energizer and a viscometer. The treating fluid has a gel. The energizer is capable of energizing a sample of the gel. The viscometer is capable of measuring a viscosity of the energized sample. The viscosity of the sample is predictive downhole viscosity of the treating fluid. The predicted downhole viscosity may be used to improve downhole viscosity. After the downhole viscosity is predicted, a concentration modification fluid can be added to cause the predicted viscosity to approach a desired viscosity.

10 Claims, 4 Drawing Sheets

REAL TIME VISCOMETER

BACKGROUND

Producing subterranean formations penetrated by wellbores are often treated to increase the permeabilities of the formations. One such production stimulation involves fracturing the subterranean formation utilizing a viscous treating fluid. That is, the subterranean formation or producing zone is hydraulically fractured whereby one or more cracks or fractures are created therein.

Hydraulic fracturing is typically accomplished by injecting the viscous treating fluid, which may have a proppant such as sand or other particulate material suspended therein, into the subterranean formation or zone at a rate and pressure sufficient to cause the creation of one or more fractures in the desired zone or formation. The treating fluid must have a sufficiently high viscosity to retain the proppant material in suspension as the treating fluid flows into the created fractures. The proppant material functions to prevent the formed fractures from closing upon reduction of the hydraulic pressure which was applied to create the fracture in the formation or zone whereby conductive channels remain in which produced fluids can readily flow to the wellbore upon completion of the fracturing treatment. There are a number of known treating fluids that may be utilized including water-based liquids containing a gelling agent comprised of a polysaccharide, such as for example guar gum.

Viscous treating fluids used in the hydraulic fracturing of petroleum reservoirs and other applications of viscous treating fluids often require field analysis of the predicted viscosity of the treating fluid as a quality control check and as a parameter useful in designing a fracturing operation or the like. Determining the downhole viscosity of the treating fluid prior to deployment of the treating fluid is desirable. Current commercially available viscometers and heat exchangers all suffer from various problems of lack of readability, lack of accuracy, slow response times, and high cost. More particularly, it is difficult to predict the downhole viscosity of treating fluids having a changing viscosity, such as used in hydraulic fracturing operations. One way to determine downhole viscosity prior to deployment is to wait until the entire volume of treating fluid reaches the desired downhole viscosity, for example, through "batch mixing." This involves the use of a holding tank and a wait of several minutes. However, today's environment calls for mixing on the fly. Time is critical, and waiting for the treating fluid to reach the downhole viscosity is time consuming, impractical, and uneconomical. Additionally, the holding tank requires cleaning and transportation from the site after the job is complete. Previously, the treating fluid was premixed, requiring cleaning of an even greater number of tanks. Another alternative is to force the treating fluid to become more viscous. However, this generally requires significant energy, and is thus costly. Lastly, viscosity curves can project an expected downhole viscosity based on initial viscosity readings. However, field analysis of treating fluids having a changing viscosity, such as used in hydraulic fracturing operations, is somewhat unreliable using the conventional viscometers. In particular, when the initial viscosity is low, conventional viscometers have a high margin of error. Accurate alternatives for measuring low viscosity are expensive and prone to damage in normal field conditions.

SUMMARY

The present invention relates generally to a viscometer. More specifically, the present invention relates to a viscometer for measuring the predicted viscosity of a treating fluid.

In one embodiment of the present invention, an apparatus for predicting a downhole viscosity of a treating fluid comprises an energizer and a viscometer. The treating fluid comprises a gel. A sample of the gel is delivered into the energizer. The viscometer is in fluid communication with the energizer and is adapted to measure the viscosity of the sample of the gel.

In another embodiment of the present invention, a method for predicting a downhole viscosity of a treating fluid comprises obtaining a sample, energizing the sample, and measuring the viscosity of the energized sample. The treating fluid comprises a gel. The viscosity of the sample is predictive of the downhole viscosity of the treating fluid.

In yet another embodiment of the present invention, an apparatus for predicting a downhole viscosity of a treating fluid comprises a means for energizing a sample of gel and a means for measuring the viscosity of the energized sample. The viscosity of the sample is predictive of the downhole viscosity of the treating fluid.

In still another embodiment of the present invention, a method for improving a downhole viscosity of a treating fluid comprises predicting the downhole viscosity of the treating fluid, determining a composition and quantity of concentration modification fluid, and adding the concentration modification fluid.

DETAILED DESCRIPTION

Figure 1:
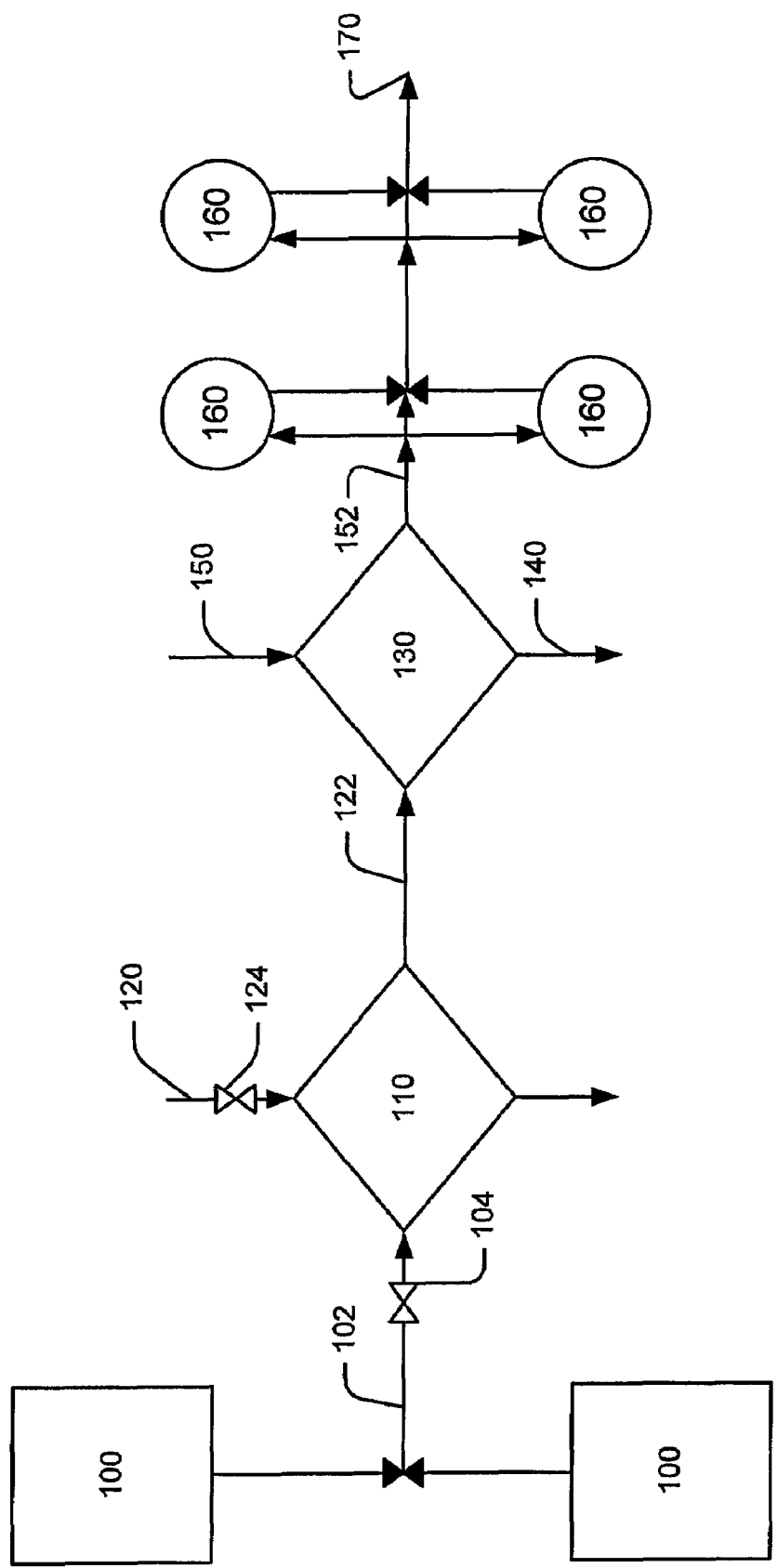
FIG. 1 is a schematic view of a typical well stimulation operation.

Referring now to FIG. 1, a typical well stimulation operation has one or more water tanks 100. A stream of water 102 passes from the one or more water tanks 100 into a pre-gel blender 110. The pre-gel blender 110 mixes the water with a polymer 120 creating a gel 122, which passes into a blender 130. Sand 140 and other additives 150 may also enter the blender 130. The sand 140 and additives 150 mix with the gel 122 to make a treating fluid 152, which then passes into a wellhead 170. Pump trucks 160 may pump the treating fluid 152, so the entire process takes only a few minutes.

While full hydration of the gel 122 (and thus, the treating fluid 152) can currently occur in less than an hour, it still takes longer than the few minutes that mixing and pumping require. Therefore, the gel 122 does not have time to become fully hydrated prior to entry into the wellhead 170. This means that downhole viscosity of the gel 122 remains unknown until after the treating fluid 152 containing the gel 122 has entered the wellhead 170.

The gel 122 is not always mixed in ideal conditions, and the gel 122 may be incorrectly mixed. A faulty water valve 104, a faulty polymer valve 124, a bad connection, or any of a number of other reasons may cause incorrect mixing. It is impractical to recapture the treating fluid 152, which contains the gel 122, after entry into the wellhead 170. Additionally, after entering the wellhead 170, it is difficult to uniformly modify the composition of the treatment fluid 152. Prediction of the downhole viscosity may allow time for adjustments prior to pumping substantial quantities of treatment fluid 152. For instance, the pumps 160 can be stopped, or other modifications can be made. It is advantageous to make modifications, such as adding water 102 and/or polymer 120, or any other concentration modification fluid prior to the deployment of the treating fluid 152 into the wellhead 170. The concentration modification fluid may be a diluting fluid added to a more concentrated fluid, or it may be a concentrating fluid added to a more diluted fluid.

Figure 2:
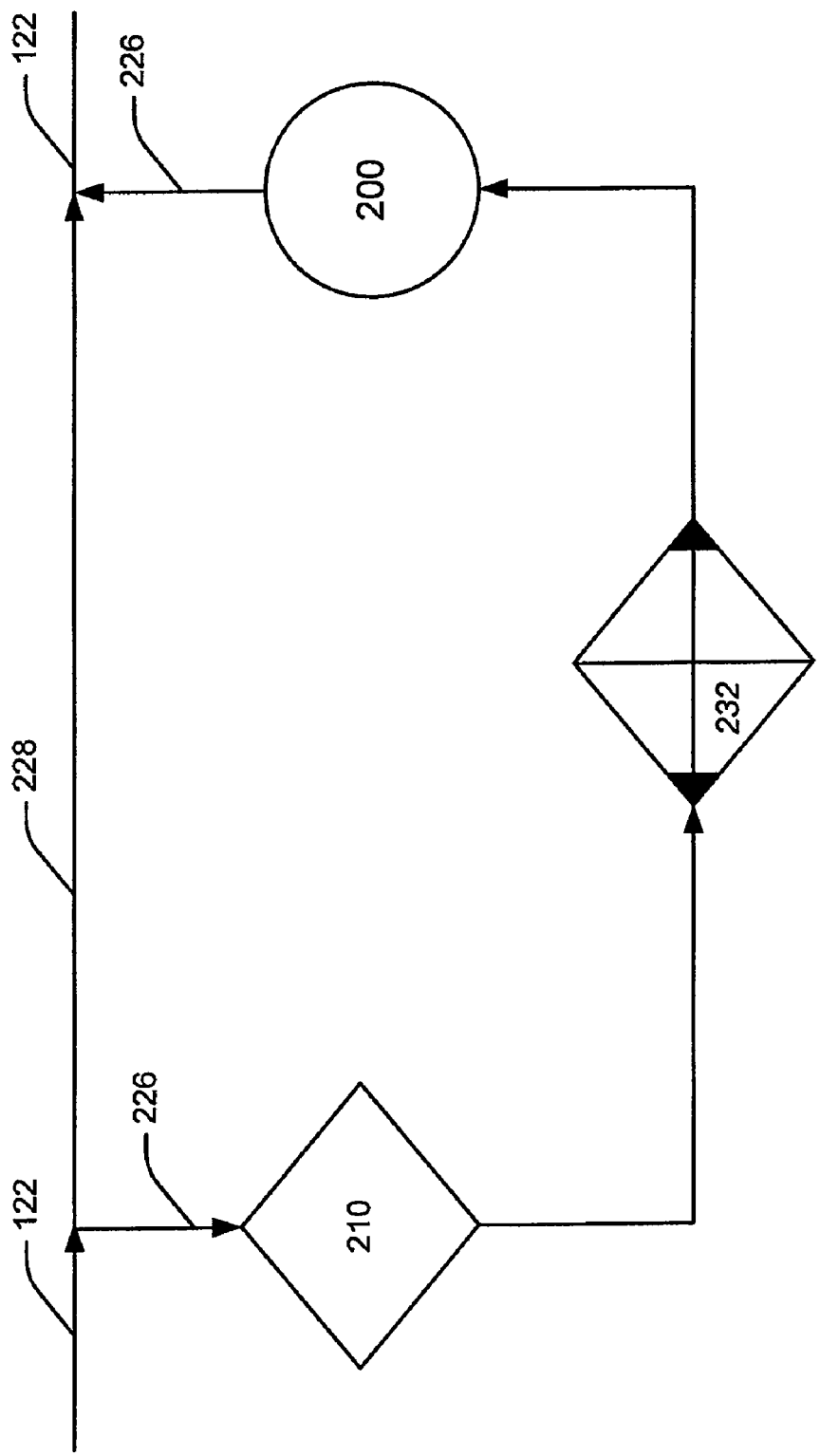
FIG. 2 is a schematic view of an apparatus for predicting downhole viscosity in accordance with an exemplary embodiment of the present invention.

Referring now to FIG. 2, the downhole viscosity of the treating fluid 152 may be predicted using a sample 226 of the gel 122, an energizer 210, and a viscometer 200. Predicting the downhole viscosity prior to the entry of the treating fluid 152 into the wellhead 170 allows time for cessation of pumping and/or modification using the concentration modification fluid, should these actions be desirable.

The sample 226 may be drawn or otherwise obtained from the gel 122, preferably between the pre-gel blender 110 and the blender 130. For example, the sample 226 may be drawn at or near the exit from the pre-gel blender 110. The gel not being sampled 228 continues to the blender 130. Taking the sample 226 near the pre-gel blender 110 allows for analysis of the sample 226 while the gel not being sampled 228 is blended with the sand 140 and other additives 150, prior to pumping the treating fluid 152 into the wellhead 170.

An energizer 210 energizes the sample 226, causing accelerated or premature hydration. In other words, the sample 226 hydrates more quickly than the gel not being sampled 228. Therefore, the viscosification of the prematurely hydrated sample 226 is more advanced than that of the gel not being sampled 228, i.e., the viscosity of the prematurely hydrated sample 226 typically increases more rapidly than the viscosity of the gel not being sampled 228. That is, the prematurely hydrated sample 226 gives a preview of the downhole viscosity of the gel not being sampled 228 (and thus, the treating fluid 152).

The energizer 210 may be anything capable of accelerating the hydration of the sample 226. For example, the energizer 210 may be a shear device (e.g. silsverson 100), an ultrasonic or sonic radiation device (e.g. Heilsher UIP 1000), a microwave generating device (e.g. GE Model JES1456WF001), a cavitator (e.g. Hydrodynamic shockwave pump), a heat exchanger, or other equivalent device. Shear producing devices may include pipes through which the sample 226 is pumped, spinning blades, or any mechanical or other device that imparts a shear force to the sample 226.

The viscometer 200 measures the viscosity of the prematurely hydrated sample 226. The viscometer 200 may be of any type. For example, the viscometer may be a Brookfield Model TT-100, or any other viscometer. In some instances, the viscometer 200 may also energize the sample 226, i.e., the viscometer 200 may also act as the energizer 210. In this instance, the separate energizer 210 is not required.

While energizing the sample 226 causes accelerated hydration and thus tends to increase viscosity, it may also cause heating of the sample 226, which tends to reduce viscosity. Thus, in order to get a better viscosity reading, the sample 226 may optionally be cooled prior to entering the viscometer 200. Cooling may be done via a heat exchanger or any other cooling device 232. Cooled fluid is easier to measure, as the viscosity is typically higher. Additionally, cooling the sample 226 allows viscosity measurement at or near room temperature, which is how viscosity measurements are typically taken. While viscosity measurements may be taken at higher temperatures, this requires adjustment to compensate for the temperature. Taking the measurement at or near room temperature reduces the need to adjust the measurement, reducing the likelihood of error in that adjustment.

The prematurely hydrated sample viscosity may be used to predict the downhole viscosity of the gel not being sampled 228. If the sample 226 is fully hydrated, the viscosity of the sample 226 may be equal to the fully hydrated downhole viscosity of the gel not being sampled 228. Alternatively, depending on the level of hydration of the sample 226, the viscosity of the sample 226 may represent some other downhole viscosity of the gel not being sampled 228. For instance, the viscosity of the sample 226 after 15 to 20 seconds may be equivalent to the viscosity of the gel not being sampled 228 after 4 to 5 minutes.

Currently, standard viscosity curves may accurately predict the downhole viscosity of the gel 122 based on the viscosity of the gel 122 after as few as 4 to 5 minutes. However, as indicated above, the gel 122 is frequently pumped into the wellhead 170 quickly, such that the downhole viscosity is not known until after the gel 122 has been pumped. While the same curves may be used to predict downhole viscosity earlier than 4 to 5 minutes, these predictions have a large margin of error. Larger viscosity readings have a lower margin of error, and the accuracy of the prediction based on the curve increases as viscosity increases. Therefore, 4 to 5 minutes typically provides an acceptable accuracy. Since the viscosity of the sample 226 after 15 to 20 seconds may be equivalent to the viscosity of the gel not being sampled 228 after 4 to 5 minutes, the downhole viscosity of the gel 122 (and thus, the treating fluid 152) may be accurately predicted based on the viscosity of the prematurely hydrated sample 226 in as little as 15 to 20 seconds.

Therefore, instead of pumping the gel 122 for 4 to 5 minutes, without knowing whether the downhole viscosity of the gel 122 will be suitable, pumping may only occur for 15 to 20 seconds before the predicted downhole viscosity is determined. This may allow only a small amount of incorrectly mixed gel 122 to enter the wellhead 170. Depending on the speed at which pumping occurs, the incorrectly mixed gel 122 may never even enter the wellhead 170.

Figure 3:
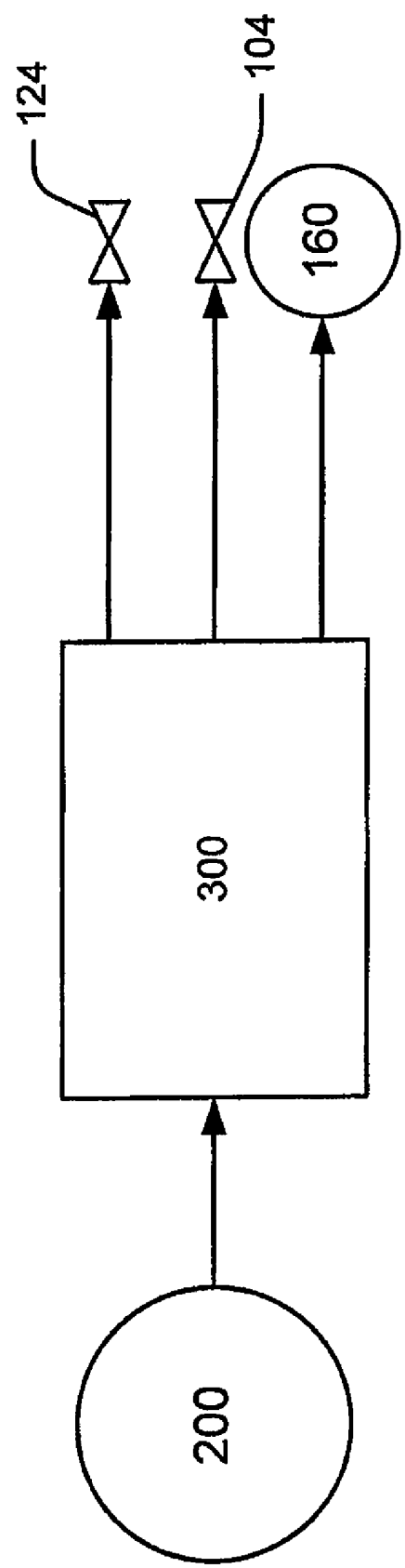
FIG. 3 is a schematic view of a computer for use with an exemplary embodiment of the present invention.

Referring now to FIG. 3, a computer 300 may be used to perform calculations associated with predicting viscosity, as well as calculations associated with adjusting viscosity. The viscometer 200 may provide viscosity information to the computer 300 through an electrical connection. The computer 300, in turn, may calculate predicted downhole viscosity and compare the prediction with the desired downhole viscosity. If the prediction and the desired downhole viscosity are inconsistent, the computer 300 may cause cessation of the pumping of the gel 122 into the wellhead 170. This may be done by directing the pumps 160 to stop pumping. Additionally, the computer 300 may calculate the composition and/or the quantity of a concentration modification fluid to add in order to bring the predicted downhole viscosity closer to the desired downhole viscosity. The computer 300 may control the water valve 104, and/or the polymer valve 124, such that the concentration modification fluid is formed within the pre-gel blender 110, and may then be added to the gel 122 to obtain a desired predicted downhole viscosity.

Figure 4:
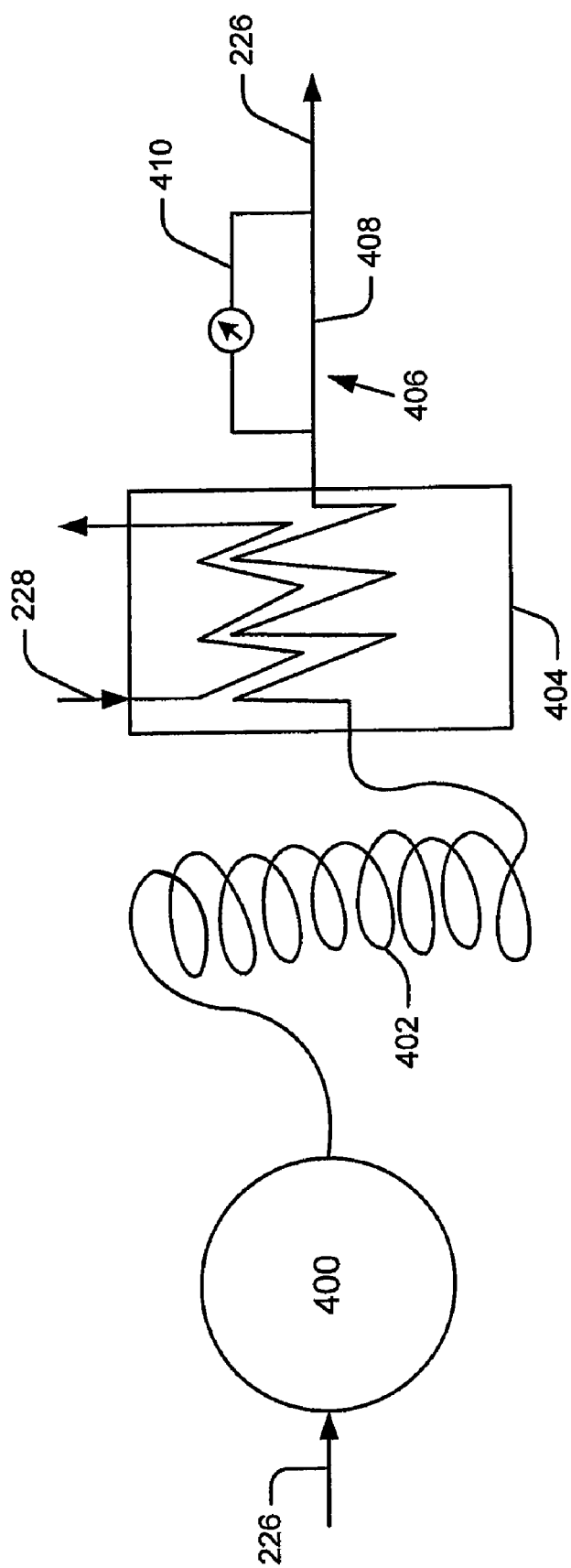
FIG. 4 is a schematic view of another embodiment of the present invention.

Referring now to FIG. 4, in one embodiment, a sample pump 400 directs the sample 226 through a high shear loop 402 for hydration, then through a heat exchanger 404 using the gel not being sampled 228 as the coolant, and then into a pipe viscometer 406. The viscometer 406 has a pipe 408 and a pressure drop transducer 410. The pipe 408 may be straight or coiled. The sample pump 400 is nearly pulseless and the flow rate is capable of being controlled accurately. For example, a dual action syringe pump may connect to a servo motor to give excellent rate control and create periodic pulses, which can be filtered out. Because the viscometer 406 can run at high pressure, air entrained in the sample 226 will collapse, providing a more accurate viscosity reading. The viscosity is easily calculable from the rate and pressure drop. The high shear loop 402 may be heated either electrically or with a hot fluid. The high shear loop 402 may be a section of small diameter pipe, which would give a large pressure drop hence the high shear and friction heating. For example, the high shear loop 402 may be constructed from 1/8" tubing. The combination of high shear and heat causes the sample 226 to hydrate quickly prior to entry into the viscometer 406. Because the flow rate is low, the entire system is small and the energy requirements are low. The only moving parts are the pump 400 and pressure transducer 410, both of which are very reliable. While the high shear loop 402 is disclosed herein as separate from the heat exchanger 404, the high shear loop 402 and the heat exchanger 404 may be the same section.

An apparatus was created to partially test the validity of one embodied approach. The material tested was a fully hydrated guar gel of various polymer concentrations. A lab syringe pump drove the gel through a small diameter pipe at various rates. The resulting viscosity data was compared to Fann 35 data at 511 l/s. As shown in the table below the agreement was excellent.

| WG-35 Conc (ppt) | Pipe Viscosity (cP) | Fann35 Viscosity (cP) | Difference (cP) | Pipe n' | Fann n' |
|---|---|---|---|---|---|
| 10 | 4.63 | 5.4 | 0.77 | 0.87 | 0.79 |
| 20 | 12.19 | 12.6 | 0.41 | 0.65 | 0.6 |
| 30 | 23.54 | 23.8 | 0.26 | 0.5 | 0.46 |
| 40 | 38.07 | 38 | −0.07 | 0.41 | 0.39 |
| 50 | 56.15 | 55.4 | −0.75 | 0.34 | 0.34 |

This technology is useful in fracturing operations and may mount on a blender, liquid gel concentrate ("LGC") blender, or high shear mixer trailers, while operating reliably in the field. It may also mount in QC vans or be used in a lab.

While the sample 226 is described generally as a discrete portion of the gel 122, continuous sampling is possible, and the term "sample" is intended to cover any portion of the gel 122 that passes through the energizer 210 and/or the viscometer 200. For example, the sample 226 may be taken after the gel 122 has been mixed with the sand 140 and other additives 150. In other words, the sample 226 of the gel 122 may include sand 140, and/or other additives, in addition to the gel 122. After passing through the energizer 210 and/or the viscometer 200, the sample 226 may be combined with the gel not being sampled 228, or it may be otherwise moved from the energizer 210 and/or the viscometer 200. Then, if desired, another sample may be taken. The sampling may alternatively be continuous.

The term "downhole viscosity" may refer to the viscosity of the gel 122 or the treating fluid 152 after full hydration, after 90% hydration, or at any other point where the viscosity is further along the viscosity curve than the initial viscosity of the gel 122.

The term "treating fluid" may refer to any fluid that may be used in a subterranean application in conjunction with a desired function and/or for a desired purpose. The term "treating fluid" does not imply any particular action by the fluid or any component thereof.

The term "gel," as used herein, and its derivatives refers to any colloidal dispersion, and the like.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. An apparatus for predicting a downhole viscosity of a treating fluid comprising a gel, the apparatus comprising:
    an energizer into which a sample of the gel is delivered;
    a viscometer in fluid communication with the energizer, said viscometer adapted to measure the viscosity of the energized sample of the gel; and
    a computer electrically connected to the viscometer and adapted to receive a signal indicative of the viscosity of the sample of the gel, wherein the computer is connected to one or more valves to control the amount of polymer being mixed with water to form the gel.

2. The apparatus of claim 1, further comprising a cooling device disposed between the energizer and the viscometer.

3. The apparatus of claim 2, wherein the cooling device comprises a heat exchanger.

4. The apparatus of claim 3, wherein the heat exchanger uses some of the gel not being sampled as a coolant.

5. The apparatus of claim 1, wherein the energizer comprises a small diameter heated high shear pipe.

6. The apparatus of claim 1, wherein the viscometer comprises a dual action syringe pump connected to a servo motor.

7. A method for predicting a downhole viscosity of a treating fluid comprising a gel, the method comprising the steps of:
    obtaining a sample of the gel;
    energizing the sample of the gel;
    measuring the viscosity of the energized sample of the gel; and
    cooling the energized gel; wherein the viscosity of the energized sample of the gel is predicative of the downhole viscosity of the treating fluid;
    and determining a composition and quantity of a concentration modification fluid that will cause the predicted downhole viscosity of the treating fluid to approach a desired downhole viscosity.

8. The method of claim 7, wherein the step of cooling is performed prior to the step of measuring the viscosity.

9. The method of claim 7, wherein the concentration modification fluid comprises water.

10. The method of claim 7, wherein the concentration modification fluid comprises a polymer.

* * * * *